United States Patent [19]

Hoerrmann

[11] Patent Number: 5,665,371

[45] Date of Patent: Sep. 9, 1997

[54] MEDICINES WHICH CONTAIN DERIVATIVES OF PROLINE OR HYDROXYPROLINE

[76] Inventor: Wilhelm Hoerrmann, Staltacherstrasse 34, Iffeldorf, Germany, D-82392

[21] Appl. No.: 763,346

[22] Filed: Dec. 11, 1996

Related U.S. Application Data

[63] Continuation of Ser. No. 370,842, Jan. 10, 1995, abandoned, which is a continuation-in-part of Ser. No. 152,097, Nov. 15, 1993, abandoned, which is a continuation of Ser. No. 875,189, Apr. 29, 1992, abandoned, which is a continuation of Ser. No. 544,177, Jun. 26, 1990, abandoned, which is a continuation of Ser. No. 375,675, Jul. 5, 1989, abandoned, which is a continuation of Ser. No. 17,254, filed as PCT/EP86/00304, May 20, 1986, abandoned.

[30] Foreign Application Priority Data

May 20, 1985 [DE] Germany .................... 35 18 078.1

[51] Int. Cl.⁶ .................. A61F 2/02; A61K 9/48; A61K 9/20; A61K 31/185

[52] U.S. Cl. .................. 424/423; 424/451; 424/464; 514/535; 514/553; 514/561

[58] Field of Search .................. 424/423, 451, 424/464; 514/535, 553, 561

[56] References Cited

PUBLICATIONS

"Structural Alterations within N–nitroso methyl urea induced tumours after in–vivo treatment with cis–hydroxyproline", Strum et al., *Lab. Invest.*, 4b(4), 347–354, 1981 1981.

*Primary Examiner*—Carlos A. Azpuru
*Attorney, Agent, or Firm*—Jacobson, Price, Holman & Stern, PLLC

[57] ABSTRACT

Pharmaceutical compositions which comprise, as an active substance, (N-alkyl) derivatives of proline or hydroxyproline. Such compositions are useful in the treatment of cancer.

4 Claims, No Drawings

MEDICINES WHICH CONTAIN DERIVATIVES OF PROLINE OR HYDROXYPROLINE

This is a continuation of application Ser. No. 08/370,842, filed Jan. 10, 1995 now abandoned; which in turn is a continuation-in-part of application Ser. No. 08/152,097, filed Nov. 15, 1993, abandoned; which in turn is a continuation of application Ser. No. 07/875,189, filed Apr. 29, 1992, abandoned; which in turn is a continuation of application Ser. No. 07/544,177, filed Jun. 26, 1990, abandoned; which in turn is a continuation of application Ser. No. 07/375,675, filed Jul. 5, 1989, abandoned; which in turn is a continuation of application Ser. No. 07/017,254, filed as PCT/EP86/00304, May 20, 1986, abandoned.

Till now chemotherapeutic treatment of cancer, especially carcinomas, is not satisfying as the therapeutic effects are very limited and the side effects are very severe. The latter is due to the fact that highly toxic substances are used, which damage not only the cancer cells but the other cells of the body also. However in the development of toxic anti-cancer-agents artificially induced animal tumors are useful as they allow some prediction as to the effects in humans.

That however is not the case of the anti-tumor-substances of the type which are in part described in this application. Their mode of action is not of an destroying nature. On the contrary they have an stabilizing, redifferentiating and positive immunological effect. And they are, characteristic for this invention, strictly specified to the alterations in human carcinomas. Their specific alterations cannot be reproduced in artificially induced animal tumors and therefore the compounds in question cannot be tested in such a way. It was nevertheless tried otherwise to perform such tests. They led not to any positive conclusions but to contradictions of the highest degree.

So in the years 1933–1946, Helen M. Dyer of the National Cancer Institute (An Index of Tumor Chemotherapy, INH 10–12, 143–144, 1949) administered a wide range of amino acids in an experimental treatment of the mouse. Among many others, she mentioned hydroxy-proline (without denominating isomers), but it is known, that with non-cytotoxic compounds, results of treatment of artificially induced animal tumors are practically untransferable to the treatment of cancer in humans.

Besides that, the results of such experimental animal tests performed with hydroxy-proline were not in agreement with one another. Positive reports of Strum et at., Lab. Invest., 46-(4): 347–354, (1981), and Lewko et at., Canc. Res., 41: 2855–2862 (1981) were decidedly contradicted by Klohe et at. J. Natl. Cancer Inst., 75 (2): 353–359 (1985) who summarized: "CHP (and AZC) did not appear to be efficacious antitumor agents." But hydroxy-proline itself is not the subject of this application, which actually are the alkyl derivatives, especially methyl derivative of hydroxy-proline. Modem biochemistry has knowledge of many examples that methylation may alter the biological properties and effects of compounds to a very high and unexpected degree. N-methyl cis (and trans) hydroxy-proline are naturally occurring substances in plants. Inigo et at., Chemical Abstracts Vol. 101, 126904, 1984).

As the main effect is of a stabilizing nature, there must be something left by the disease to be stabilized. That means that the compounds have, contrary to customary chemotherapy, less effect in the case of histologically complete immature cancer, and more in cases of middle malignancy. The medical main, but not only, indications are solid cancer, especially carcinomas of the colon and rectum and of the urinary system and their local and metastatic complications and of tumors of neuroectodermal origin, as there are astrocytomas, gliomas and melanomas.

At any rate cancer tissue should first be removed by surgery and the administration of these compounds should only follow in order to prevent cancer complications or to treat them. For the preventive administration of N-methyl-cis-4-hydroxy-L-proline is especially suitable, as the compound is not toxic. Subacute toxicity is higher than 10000 mg/kg.

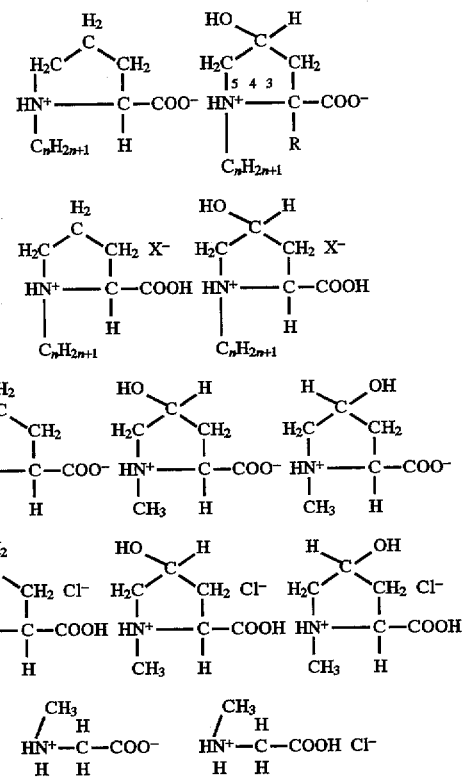

All compounds may be prepared by methods known per se.

As an example this is explained in more detail for cis- and trans-N-methyl-4-hydroxy-L-proline and their hydrochlorides:

As starting compound serves cis- or trans-4-hydroxy-L-proline, respectively, which are both known substances and which may be obtained commercially. In the following a reductive methylation is carried out in water which 1.17 eq formaldehyde solution (37%) by hydrogenation in the presence of 5% Pd on carbon at room temperature until no more $H_2$ is taken up (45 to 60 minutes).

The raw product isolated by evaporation is further purified by recrystallisation from ethanol/water 8:2.

Analysis data of N-methyl-cis-4-hydroxy-L-proline:
Aspect: practically colorless crystals in the form of needles.
Point of decomposition: at approximately 180° C. (not exactly reproducible)
Content: 99,6% (HCl $O_4$)

Analysis data of N-methyl-trans-4-hydroxy-L-proline:
Aspect: practically colorless crystals in form of needles
Point of decomposition: 239,5° to 241° C.
Content: 104% (HCl $O_4$)

The hydrochlorides of the above-mentioned compounds are obtained by dissolving the N-methyl compounds in an equivalent amount of diluted hydrochloric acid and evaporation to dryness.

Analysis data of N-methyl-4-hydroxy-L-proline-hydrochloride:
Aspect: practically colorless powder
Melting Point: 177° to 179° C.
Content: 101,1% (Ag NO$_3$)
Analysis data of N-methyl-trans-4-hydroxy-L-prolin-hydrochloride:
Aspect: practically colorless powder
Melting Point: 181° to 183° C. (decomposition)
Content: 99,6% (Ag NO$_3$)

The results which may be obtained so far therapeutically by pharmaceuticals in treating cancer and viral diseases as well as diseases of the vascular system and the nervous system are in many cases not at all satisfying, due to the fact that the effect is too low or the side effects are too severe. The object of the invention is therefore to provide a pharmaceutical or pharmaceutical composition which is able to alleviate or cure in an improved way the above-mentioned pathological alterations with less side effects. This object is solved by a pharmaceutical of the type mentioned.

The pharmaceuticals according to the invention may also contain the derivatives of proline or hydroxy-proline in the form of pharmaceutically acceptable modifications, especially as such modifications, which are converted within the body to the free form of the derivatives. Such modifications are especially alkali metal salts, earth alkali metal salts, acid addition salts, esters, amides and ethers of proline or hydroxyproline and the N-alkyl derivatives as well as oligo- and polypeptides thereof.

The pharmaceuticals according to the invention are in general administered in the same way as usual amino acids, i.e. preferably orally or intraveneously or central-intraveneously. Also the administration of tablets, dragees, solutions for injection or infusion, is the same.

The dosage also lies in the usual region as applied for amino acids; this dosage may be between 0.01 and 0.1 g/kg per day.

The contra-indications known for all amino acids are also to be observed here.

The pharmaceutical preparation and processing is carried out in a manner known per se and considers legal regulations in view of purity of the substance, sterility, freedom of pyrogen etc.

As an example for the excellent effect of the substances according to the invention against cancer cells, the following experiments with cell cultures have been carried out:

In this "stem cell assay" of an astrocytoma of human origin, the number of colonies formed by the tumor is determined. The lower with number, the stronger is the effect.

In the present experiment, sarcosine was used as a free base together with either N-methyl-cis-4-hydroxy-L-proline or N-methyl-trans-4-hyrdroxy-L-proline, both as hydrochlorides. The weight is given in micrograms.

| | |
|---|---|
| Control without any addition | 814 |
| control 10 sarc | 598 |
| 100 methyl trans + 10 sarc | 285 |
| 10 methyl trans + 1 sarc | 450 |
| 1 methyl trans + 0,1 sarc | 544 |
| 100 methyl cis + 10 sarc | 300 |
| 10 methyl cis + 1 sarc | 320 |
| 1 methyl cis + 0,1 sarc | 280 |

Results:

While the addition of sarcosine leads already to a reduction in the formation of colonies, this effect is essentially enhanced by the addition of N-methyl derivatives of hydroxyproline. As most remarkable it is to be emphasized that the cis-isomer maintains its tumorinhibiting effect completely even when the quantity of the active substance is reduced to a hundredth.

Explanation of expressions:
1. Carcinomas: Malignant tumors of epithelial origin in internal organs or the skin of adult persons.
2. Related minors: Tumors of neuroectodermal origin especially astrocytoma.

I claim:

1. A method of treating carcinomas or tumors of neuroectodermal origin selected from a group consisting of astrocytomas, gliomas and melanomas in a human patient, comprising administration to said patient orally or intravenously, about 0.01 g/kg–0.1 g/kg daily, of at least one N-alkyl compound selected from the group consisting of N-methyl-hydroxy-proline, N-methyl-proline, N-ethyl-hydroxy-proline, N-ethyl-proline, N-propyl-hydroxy-proline, N-propyl-proline, N-butyl-hydroxy-proline, N-butyl-proline and pharmaceutically acceptable derivatives of said N-alkyl compounds.

2. A pharmaceutical composition for oral or intravenous administration for treating carcinomas or tumors of neuroectodermal origin selected from a group consisting of astrocytomas, gliomas and melanomas in human patients, in need thereof, said composition comprising at least one N-alkyl compound selected from the group consisting of N-methyl-hydroxyproline, N-methyl-proline, N-ethyl-hydroxyproline, N-ethyl-proline, N-propyl-hydroxyproline, N-propyl-proline, N-butyl-hydroxyproline, N-butyl-proline and pharmaceutically acceptable derivatives of said N-alkyl compounds, in a therapeutically effective amount, and a pharmaceutically acceptable carrier.

3. The composition according to claim 2 wherein the dosage of the compound is between 0.01 and 0.1 g/kg per day.

4. The composition according to claim 2 wherein the composition is in the form of tablets, dragees, solutions for injection or infusion.

* * * * *